United States Patent [19]

Wakabayashi et al.

[11] 3,939,186
[45] Feb. 17, 1976

[54] PROCESS FOR PRODUCING ETHERS OF STEROIDS

[75] Inventors: Ken-ichi Wakabayashi; Susumu Kanno, both of Machida, Japan

[73] Assignee: Mitsubishi Chemical Industries Limited, Tokyo, Japan

[22] Filed: Dec. 6, 1974

[21] Appl. No.: 530,151

[30] Foreign Application Priority Data

Dec. 29, 1973 Japan .................................. 49-1184

[52] U.S. Cl. ........................... 260/397.4; 260/397.5
[51] Int. Cl.² .......................... C07J 9/00; C07J 1/00
[58] Field of Search ................................. 260/397.5

[56] References Cited
FOREIGN PATENTS OR APPLICATIONS
813,845   8/1955   United Kingdom .............. 260/397.5

OTHER PUBLICATIONS

Elena et al., Vol. 80 CA pars, 59679h (1974) Abstract of Rom. 54,683 Feb. 20, 1973.

Primary Examiner—Elbert L. Roberts
Attorney, Agent, or Firm—Oblon, Fisher, Spivak, McClelland & Maier

[57] ABSTRACT

A process for producing a steroid ether which comprises admixing an alkali, a reactant steroid having a hydroxyl group attached directly to an aromatic ring in the steroid nucleus, and a dialkyl sulfate in the presence of at least one hydrophilic solvent in which said reactant and product steroid is readily soluble, selected from the group consisting of cyclic ether and ketone.

12 Claims, No Drawings

# PROCESS FOR PRODUCING ETHERS OF STEROIDS

BACKGROUND OF THE INVENTION

1. Field of the Invention

The present invention relates to an improved process for etherifying steroids which have a hydroxyl group attached directly to an aromatic ring.

2. Description of the Prior Art

Among conventional processes, the currently most widely used process for etherifying a phenolic hydroxyl group of steroids which have a hydroxyl group attached directly to an aromatic ring is by suspending or dissolving the phenolic hydroxyl group containing steroid into an alkaline aqueous solution, an alcoholic alkaline solution or a mixture thereof, and then adding dialkyl sulfate thereto. However, that process has the disadvantage that when the dialkyl sulfate is added into the high concentration alkaline solution, a reaction of dialkyl sulfate with alkali occurs in preference to the reaction of the dialkyl sulfate with the phenolic hydroxyl group of the steroid. A large amount of an inorganic sulfate is thus formed as a by-product to the reaction, and the desired steroid ether can be obtained in yields of only 50–70% of the theoretical. Even if the alkali and dialkyl sulfate are used in large excess amounts, the yields are still quite low. It has thus been very difficult to industrialize the conventional reaction technique.

After an elaborate study to overcome the above problems, the present inventors have found that steroids which have a hydroxyl group attached directly to an aromatic ring, and dialkyl sulfate are first admixed into a water-alcohol solvent. An alkali is then added thereto to obtain the desired product. This reaction results in improved yields of 70–97%. However, this process still has the following disadvantages:

1. At least 20 equivalents of dialkyl sulfate and alkali for the starting material steroids are necessary to obtain the desired product in such a high yield.
2. The homogeneous reaction is difficult because of the low solubilities of the reactant steroids having a phenolic hydroxyl group. Also, the obtained alkyl ethers in water-alcohol solvent result in a high slurry concentration of the reaction mixture.
3. The maximum purity of the obtained alkyl ethers is 95–97% and a further purification is required.

SUMMARY OF THE INVENTION

Accordingly, it is one object of this invention to provide a process of etherifying the phenolic hydroxyl groups of a steroid which has a hydroxyl group attached directly to an aromatic ring, in high yields, without the use of large excess amounts of dialkyl sulfate.

It is another object of this invention to provide such a high yield process wherein the reaction is conducted in a homogeneous reaction medium.

A still further object of this invention is to accomplish such an etherification process wherein further purification of the obtained alkyl ethers can be substantially eliminated.

These and other objects of this invention, as will hereinafter become more readily apparent from the following description, have been obtained by (i) adding an alkali or an alkaline solution thereof into the reactant steroids and dialkyl sulfate or (ii) adding an alkaline salt of the reactant steroids or an alkaline solution thereof into dialkyl sulfate in the presence of at least one hydrophilic solvent selected from the group consisting of cyclic ethers and ketones, which readily dissolve the obtained reactant ethers.

DETAILED DESCRIPTION OF THE PREFERRED EMBODIMENTS

It has been found that according to the process described above, ethers of steroids can be obtained in high purity and almost a quantitative yield, while employing a far smaller amount of dialkyl sulfate.

In one embodiment of the present invention, the alkali is admixed with the reactant steroid and the dialkyl sulfate, both of which are dissolved in a hydrophilic solvent. Alternately, the alkali and the reactant steroid are dissolved into the hydrophilic solvent, and this solution is admixed with the dialkyl sulfate, which is also dissolved in the hydrophilic solvent. Suitable hydrophilic solvents which may be used herein include, among others, the cyclic ethers such as dioxane, tetrahydrofuran, methyltetrahydrofuran, tetrahydropyrane or the like; the ketones such as acetone, methyl ethyl ketone, or the like. Particularly preferred solvents are tetrahydrofuran, dioxane, acetone, methyl ethyl ketone or the like. The amount of said solvent to be used is at least 0.5 parts by weight per part by weight of the reactant steroid, and preferably about 0.5 – 30 parts by weight. In addition, these solvents may contain any organic solvents other than these solvents described above, favorably hydrophilic solvents, such as alcohols.

According to the present invention, about 60% of the etherification is effectuated even if one equivalent (0.5 mol) of dialkyl sulfate per one equivalent of steroid is used. The reaction is almost quantitatively completed if at least 1–5 equivalents of dialkyl sulfate is used. Suitable dialkyl sulfates which may be used in the present invention include those wherein each alkyl group contains 1–5 carbon atoms, such as dimethyl sulfate, diethyl sulfate, dibutyl sulfate, diamyl sulfate or the like.

Suitable alkalis which may be used in the present invention include the alkaline metal or alkaline earth metal hydroxides and more preferably, the hydroxides of alkaline metals, such as sodium hydroxide, potassium hydroxide, lithium hydroxide or the like. These alkalis can be used either in solid form or in solution, generally in the form of an aqueous solution of 1 – 50 wt%, preferably 5–30 wt% concentration. The amount of alkali which should be used, is at least one equivalent per one equivalent of dialkyl sulfate, and generally not more than about two equivalents. The actual amount to be used usually will be that quantity necessary to decompose the undesirable dialkyl sulfate, when the alkali is admixed into the pre-mixed reactant steroids and reactant dialkyl sulfate, as process (i) above.

However, when an alkaline salt of the reaction steroids or an alkaline solution thereof is added into dialkyl sulfate as in the above process (ii), it is preferred that the amount of alkali used be initially an amount of one equivalent or a slight excess, per one equivalent of phenolic hydroxyl group in the reactant steroids. Any remaining unreacted dialkyl sulfate will be hydrolyzed by further addition of alkali. Thus, an excess amount of alkali may be initially added along with the reactant steroids. Then additional amounts of alkali, in amounts of more than one equivalent per equivalent of phenolic hydroxyl group on the reactant steroid, and less than one equivalent per equivalent of dialkyl sulfate may be used.

The reaction temperature ranges from about −5°C to about 70°C. The preferred range is from −5°C to 50°C since the rate of hydrolysis will increase at temperatures above 50°C. Although the rate of addition of the alkali is not critical, normally, the alkali is added over a period of from about 5 minutes to about 5 hours. The reactant steroids which are used as a starting material for the process of the present invention include those wherein the A ring or both the A and B rings of the steroid are aromatic rings having a hydroxyl group. Representative or such steroids are estrone, estradiol or the like. The B, C and D rings, except an aromatic ring, of said steroids may have carbon-carbon double bonds and/or other etherification-inert substituents, for example, groups such as alkyl, alkenyl, alkynyl or alkoxy, namely those having up to 10 carbon atoms, acyl, nitro, oxo, halogen, amino or the like. Exemplary of the above steroids are estriol, equilin, equilenin, 16-oxoestradiol, 16-epiestriol, 17α-estradiol, 17 α-methylestradiol, 17α-ethynulestradiol, 19-nor-pregna-1,3,5(10)-triene-3-ol-20-one, 17-epiestriol, 6-dehydroestrone, 9(11)-dehydrostrone, 4-methylestra-13,5,-(10)-triene-1,17β-diol, estra-1,3,5(10)-triene-1,4,17β-triol, 4-chrolestradiol, 4-nitroestrone, 14-dehydroequilenin, 11β-hydroxyestradiol, 11β-hydroxyestrone, estra-1,3,5(10),6,8-pentaene-6-ol-17-one, estra-1,3,5(10),6,8-pentaene-6,17β-diol or the like.

The present invention makes it possible to produce ether derivatives of steroids more easily in higher purity and higher yields as compared to other known processes. Particularly, starting with estrone, estradiol or the like, the corresponding ethers of said steroids can be obtained in approximately 100% purity, thereby requiring no further purification. In addition, it is one advantage of the process of this invention that when a reaction solvent whose boiling point at atmospheric pressure is less than 100°C, such as tetrahydrofuran, acetone, methyl ethyl ketone or the like is used, the desired crystals of the steroid-alkyl ethers suspended in water are obtained only by removing the solvent after completion of etherification. The obtained crystals are then collected by filtration and washed with water to easily form the desired steroid ethers in high purity and high yield. As has been previously described in detail, the present invention is a process which makes it possible to obtain ethers in high yields and approximately 100% purity, which requires no further purification. The process of the present invention thus has many advantages, particularly in reducing production costs and in saving the very expensive reaction steroids used as starting materials.

Having generally described the invention, a more complete understanding can be obtained by reference to certain specific examples, which are included for purposes of illustration only and are not intended to be limiting unless otherwise specified.

The purity of the product shown in the Examples and the Comparative Examples were determined by gas chromatography, and the yields are shown as those for the theoretical yields based upon the reactant steroids.

EXAMPLE 1

Into a mixture of 1 g of estrone, 0.5 ml of dimethyl sulfate and 5 ml of tetrahydrofuran, 6 ml of 10% aqueous solution of potassium hydroxide was added over a period of one hour. The reaction temperature was maintained at 15° − 20°C during the addition. The resulting mixture was stirred for one hour to complete the etherification. Then, 6 ml of water was added, and tetrahydrofuran was distilled under atmospheric pressure. The crystals which formed during the distillation were filtered from the cooled reaction mixture, washed with water and dried to obtain 1.048 g of the 100% purity methyl ether of estrone in a 99.7% yield.

COMPARATIVE EXAMPLE 1

Into a mixture of 20 ml of methanol and 16 ml of 30% aqueous solution of potassium hydroxide, 1.0 g of estrone was dissolved and the mixture was cooled in an ice bath and stirred while 4 ml of dimethyl sulfate was added. Stirring was continued for 2 hours. Water was added to the reaction mixture and the crystals which precipitated during the addition of water were filtered, washed with water and dried to obtain 0.341 g of the 96.3% purity methyl ether of estrone in a 34.2% yield.

COMPARATIVE EXAMPLE 2

Into a mixture of 20 ml of methanol and 4 ml of dimethyl sulfate, 1.0 g of estrone was suspended and the mixture was cooled in an ice bath and stirred while 16 ml of 30% aqueous solution of potassium hydroxide was added over a period of 1 hour. Stirring was continued for 2 hours. Water was added to the reaction mixture, and the precipitated crystals were filtered, washed with water and dried to obtain 1.017 g of the 96.0% purity methyl ether of estrone in a 96.7% yield.

EXAMPLE 2

Example 1 was repeated except that 5 ml of acetone was used instead of tetrahydrofuran. 1.042 g of the 100% purity methyl ether of estrone was obtained in a 99.3% yield.

EXAMPLE 3

Into a mixture of 1 g of estrone, 0.5 ml of dimethyl sulfate and 5 ml of tetrahydrofuran, 6 ml of 10% methanolpotassium hydroxide solution was added over a period of 1 hour. The reaction temperature was maintained at 10° − 15°C. The resulting mixture was stirred for one hour to complete the etherification. Then, 15 ml of water was added to the reaction mixture, tetrahydrofuran and methanol were distilled off under atmospheric pressure. The residue was extracted with chloroform, washed with water, and dried. Evaporation of chloroform yielded 1.032 g of the 100% purity methyl ether of estrone in a 98.4% yield.

EXAMPLE 4

Into a mixture of 0.39 ml of dimethyl sulfate and 5 ml of tetrahydrofuran, 1 g of estrone and 0.76 ml of 30% KOH aqueous solution dissolved in 5 ml of tetrahydrofuran were added over a period of one hour. The reaction temperature was maintained at 15° − 20°C. The resulting mixture was stirred for one hour. Then, after the addition of 10 ml of 1% KOH aqueous solution, Example 1 was repeated to obtain 1.049 g of the 100% purity methyl ether of estrone in a 99.8% yield.

EXAMPLE 5

Example 4 was repeated except that 1 ml of 20% NaOH aqueous solution was used instead of 30% KOH aqueous solution. 1.046 g of the 100% purity methyl ether of estrone was obtained for a 99.5% yield.

EXAMPLE 6

Example 1 was repeated except that diethyl sulfate was used instead of dimethyl sulfate. 1.082 g of the 100% purity ethyl ether of estrone was obtained in a 98.2% yield.

EXAMPLE 7

Into a mixture of 1 g of estrone, 0.5 ml of dimethyl sulfate and 5 ml of dioxane, 5 ml of 10% NaOH aqueous solution was added over a period of one hour. The reaction temperature was maintained at 15° – 20°C. The resulting mixture was stirred for one hour. Then, 30 ml of water was added and the resulting cyrstals were filtered, washed with water and dried to obtain 1.040 g of the 100% purity methyl ether of estrone in a 98.9% yield.

EXAMPLE 8

Into a mixture of 1 g of estrone, 0.5 ml of dimethyl sulfate and 10 ml of methyl ethyl ketone, 5 ml of the 10% NaOH aqueous solution was added over a period of one hour. The reaction temperature was maintained at 15° – 20°C. The resulting mixture was stirred for 1 hour. 10 ml of water was added to the reaction mixture and methyl ethyl ketone was distilled off. The crystals which formed during the distillation were filtered from the cooled reaction mixture, washed with water and dried to obtain 1.037 g of the 100% purity methyl ether of estrone in a 98.6% yield.

EXAMPLES 9–13

Except that estrone in Example 1 was replaced respectively by estradiol, ethynylestradiol, estriol, 1-methylestrone, and equilenin, Example 1 was substantially repeated. The reaction conditions and the results are shown in Table 1 below.

Table 1

| Example No. | Starting Materials and the amount to be used Steroids | (g) | THF (ml) | Dimethyl sulfate (ml) | 30% KOH (ml) | Reaction temp. (°C) | Yield (g) (%) | Purity (%) |
|---|---|---|---|---|---|---|---|---|
| 9 | Estradiol | 1.0 | 10 | 0.5 | 2.0 | 15–20 | (1.032g) 98.1 | 100 |
| 10 | Ethynyl estradiol | " | 10 | " | " | " | (1.040g) 99.2 | 100 |
| 11 | Estriol | " | 20 | " | " | " | (0.948g) 90.3 | 99 |
| 12 | 1-methyl-estrone | " | 10 | " | " | " | (1.045g) 99.6 | 100 |
| 13 | Equilenin | " | 10 | " | " | " | (1.008g) 95.8 | 100 |

THF: tetrahydrofuran

EXAMPLES 14–16

Except that the reaction temperature in Example 1 was replaced respectively by 30°C, 40°C and 60°C, Example 1 was repeated. The reaction condition and the results are shown in Table 2 below.

TABLE 2

| Example No. | Starting Materials and the amount to be used Steroids | (g) | THF (ml) | Dimethyl sulfate (ml) | 10% KOH (ml) | Reaction temp. (°C) | Yield (g) (%) | Purity (%) |
|---|---|---|---|---|---|---|---|---|
| 14 | Estrone | 1.0 | 5 | 0.5 | 6.0 | 30 | (1.052g) 100 | 99.7 |
| 15 | " | " | " | " | " | 40 | (1.056g) 100 | 99.6 |
| 16 | " | " | " | " | " | 60 | (1.044g) 96.7 | 97.2 |

COMPARATIVE EXAMPLES 3–7

Except that estrone in Comparative Example 1 was replaced by respectively estradiol, ethynylestradiol, estriol, 1-methylestrone, and equilenin, Comparative Example 1 was substantially repeated. The reaction conditions and the results are shown in Table 3 below.

TABLE 3

| Comparative Example No. | Starting Materials and the amounts to be used Steroids | (g) | Methanol (ml) | Dimethyl sulfate (ml) | 30% KOH (ml) | Reaction temp. | Yield (g) (%) | Purity (%) |
|---|---|---|---|---|---|---|---|---|
| 3 | Estradiol | 1.0 | 20 | 4 | 16 | in ice bath | (0.302g) 30.4 | 95.8 |
| 4 | Ethynyl-estradiol | " | " | " | " | " | (0.138g) 13.2 | 96.9 |
| 5 | Estriol | " | " | " | " | " | 0 | — |
| 6 | 1-methyl- | | | | | | | |

TABLE 3-continued

| Comparative Example No. | Starting Materials and the amounts to be used | | Methanol (ml) | Dimethyl sulfate (ml) | 30% KOH (ml) | Reaction temp. | Yield (g) (%) | Purity (%) |
|---|---|---|---|---|---|---|---|---|
| | Steroids | (g) | | | | | | |
| | estrone | '' | '' | '' | '' | '' | (0.341g) 32.5 | 97.0 |
| 7 | Equilenin | '' | '' | '' | '' | '' | (0.331g) 31.4 | 96.8 |

COMPARATIVE EXAMPLES 8–12

Except that estrone in Comparative Example 2 was replaced similarly to the above Examples 3–7 respectively, Comparative Example 2 was substantially repeated. The reaction conditions and the results are shown in Table 4 below.

TABLE 4

| No. | Starting Materials and amount | | Methanol (ml) | Dimethyl sulfate (ml) | 30% KOH (ml) | Reaction temp. | Yield (g) (%) | Purity (%) |
|---|---|---|---|---|---|---|---|---|
| | Steroids | (g) | | | | | | |
| 8 | Estradiol | 1.0 | 20 | 4 | 16 | in ice bath | (0.952g) 90.4 | 97.0 |
| 9 | Ethynyl-estradiol | '' | '' | '' | '' | '' | (1.019g) 97.2 | 97.1 |
| 10 | Estriol | '' | '' | '' | '' | '' | (0.791g) 75.3 | 96.0 |
| 11 | 1-methyl-estrone | '' | '' | '' | '' | '' | (1.012g) 96.5 | 96.9 |
| 12 | Equilenin | '' | '' | '' | '' | '' | (0.930g) 88.4 | 97.1 |

When the results of the Examples of the present invention are compared with those of the Comparative Examples of the conventional processes, it will be apparent that the process of the present invention produces quite outstanding results making it possible to produce steroid ethers of very high purity (approaching 100%) and high yield.

Having now fully described the invention, it will be apparent to one of ordinary skill in the art that many changes and modifications can be made thereto without departing from the spirit or scope of the invention as set forth herein.

What is claimed as new and intended to be covered by letters Patent is:

1. A process for producing estrogenic steroid ethers which comprises admixing an alkali, a reactant estrogenic steroid having a hydroxyl group attached directly to an aromatic ring of the estrogenic steroid nucleus and a dialkyl sulfate in the presence of a hydrophilic solvent selected from the group consisting essentially of dioxane, tetrahydrofuran, methyltetrahydrofuran, tetrahydropyrane, acetone, and methyl ethyl ketone, in which said reactant and product estrogenic steroid are readily soluble.

2. The process of claim 1, wherein said alkali is added to a solution of reactant estrogenic steroid and said dialkyl sulfate dissolved in said hydrophilic solvent.

3. The process of claim 1, wherein a solution of said alkali and said reactant estrogenic steroid, dissolved in said hydrophilic solvent, is added to a solution of said dialkyl sulfate dissolved in said hydrophilic solvent.

4. The process of claim 1, wherein said reactant estrogenic steroid is selected from the group consisting of estrone, estradiol, ethynylestradiol, estriol, 1-methylestrone and equilenin.

5. The process of claim 1, wherein said dialkyl sulfate is selected from the group consisting of dimethyl sulfate, diethyl sulfate, dibutyl sulfate and diamyl sulfate.

6. The process of claim 1, wherein said alkali is selected from the group consisting of sodium hydroxide, potassium hydroxide and lithium hydroxide.

7. The process of claim 1, wherein said hydrophilic solvent is dioxane.

8. The process of claim 1, wherein at least 1.5 equivalents of dialkyl sulfate per one equivalent of said reactant steroid is used.

9. The process of claim 1, wherein said alkali is present in amounts of from 1–2 equivalents per one equivalent of dialkyl sulfate.

10. The process of claim 1, wherein said hydrophilic solvent is used in amounts of from 1 – 30 parts by weight per one part by weight of the starting material.

11. The process of claim 1, wherein said etherification is carried out at a temperature of from −5°C to 50°C.

12. The process of claim 2, wherein said alkali is added as a 5–30% aqueous solution.

* * * * *

United States Patent and Trademark Office
CERTIFICATE OF CORRECTION

PATENT NO. : 3939186
DATED : February 17, 1976
INVENTOR(S) : Ken-ichi Wakabayashi and Susumu Kanno It is certified that error appears in the above-identified patent and that said Letters Patent are hereby corrected as shown below:

Column 3, line 11, "or" should read --of--;

Line 20, "17 $\alpha$ -ethylnulestradiol" should read --17 $\alpha$ --ethynylestradiol--

Line 22, "9(11)-dehydrostrone" should read --9(11)-lehydroestrone--;

Also in Line 22, "4-methylestra 13,5-" should read --4-lethylestra -1,3,5---;

Line 24, "4-chrolestradiol" should read --4-chloroestradiol--.

Column 4, lines 40-41, "methanolpotassium" should read --methanol-potassium--;

And line 68, "for" should read --in--.

In Table 1, on column 5 and 6, "Ethynyl" should read --Ethynyl- --.

Signed and Sealed this

Ninth Day of November 1976

[SEAL]

Attest:

RUTH C. MASON
Attesting Officer

C. MARSHALL DANN
Commissioner of Patents and Trademarks